United States Patent [19]
Upchurch et al.

[11] Patent Number: 5,948,965
[45] Date of Patent: Sep. 7, 1999

[54] SOLID STATE CARBON MONOXIDE SENSOR

[75] Inventors: Billy T. Upchurch, Virginia Beach; George M. Wood, Newport News; David R. Schryer, Hampton; Bradley D. Leighty, Newport News; Donald M. Oglesby, Virginia Beach; Erik J. Kielin, Norfolk; Kenneth G. Brown, Virginia Beach, all of Va.; Christine M. D'Ambrosia, Henrietta, N.Y.

[73] Assignee: The United States of America as represented by the Administrator of the National Aeronautics and Space Administration, Washington, D.C.

[21] Appl. No.: 08/845,899

[22] Filed: Apr. 28, 1997

Related U.S. Application Data

[60] Provisional application No. 60/016,669, May 1, 1996.

[51] Int. Cl.$^6$ .............................. G01N 27/12; G01N 7/00; B01J 23/40
[52] U.S. Cl. ........................ 73/23.31; 73/25.01; 73/31.05; 422/88; 422/97
[58] Field of Search ................................ 73/23.31, 31.06, 73/31.01, 31.05, 25.01, 422; 422/88, 96, 97, 98

[56] References Cited

U.S. PATENT DOCUMENTS

| | | |
|---|---|---|
| 3,959,764 | 5/1976 | Allman ........................................ 338/34 |
| 4,123,225 | 10/1978 | Jones et al. ................................. 422/98 |
| 4,126,580 | 11/1978 | Lauder ...................................... 252/462 |
| 4,421,720 | 12/1983 | Kamiya ...................................... 422/97 |
| 4,817,414 | 4/1989 | Hagen et al. ................................. 73/25 |
| 4,818,977 | 4/1989 | Alexander ................................. 340/633 |
| 5,017,340 | 5/1991 | Pribat et al. ............................... 422/98 |
| 5,055,269 | 10/1991 | Palumbo et al. ............................ 422/96 |
| 5,616,850 | 4/1997 | Sage ........................................ 73/23.31 |
| 5,629,474 | 5/1997 | Williams ................................... 73/23.2 |
| 5,635,136 | 6/1997 | Glaunsinger et al. ..................... 422/88 |

*Primary Examiner*—Hezron Williams
*Assistant Examiner*—J. David Wiggins
*Attorney, Agent, or Firm*—Hillary T. Womack

[57] ABSTRACT

A means for detecting carbon monoxide which utilizes an un-heated catalytic material to oxidize carbon monoxide at ambient temperatures. Because this reaction is exothermic, a thermistor in contact with the catalytic material is used as a sensing element to detect the heat evolved as carbon monoxide is oxidized to carbon dioxide at the catalyst surface, without any heaters or external heating elements for the ambient air or catalytic element material. Upon comparison to a reference thermistor, relative increases in the temperature of the sensing thermistor correspond positively with an increased concentration of carbon monoxide in the ambient medium and are thus used as an indicator of the presence of carbon monoxide.

6 Claims, 3 Drawing Sheets

SOLID STATE CARBON MONOXIDE SENSOR

This application claims benefit of provisional application Ser. No. 60/016,669 filed Mar. 1, 1996.

ORIGIN OF THE INVENTION

The invention described herein was jointly made by employees of the United States Government, contract employees during the performance of work under a NASA contract which is subject to the provisions of Public Law 95-517 (35 USC 202) in which the contractor has elected not to retain title, and an employee of Rochester Gas and Electric Corporation during the performance of work under a Memorandum of Agreement.

BACKGROUND OF THE INVENTION

The current invention pertains generally to the field of sensors used in the detection of carbon monoxide. In particular, this invention pertains to the use of an unheated, platinized tin-oxide catalyst in a sensor which detects the presence of carbon monoxide in the atmosphere or other oxidant-containing medium.

Since carbon monoxide is such a toxic gas, the ability to detect its presence in environmental spaces such as homes and automobiles is very important. Public awareness of this problem has produced a great demand for low priced carbon monoxide sensing devices. Sensors currently available on the market, however, exhibit extremely long response times and lack sensitivity to low concentrations of carbon monoxide. In addition, all of these low-priced sensors exhibit inordinately long recovery times after exposure to carbon monoxide.

Prior art methods utilize either complex and expensive instrumentation or devices utilizing conductance or spectroscopic techniques to detect carbon monoxide. Most detectors currently on the market are based on the change in resistance of sintered tin oxide in the presence of carbon monoxide. In addition to the problems mentioned above, the sintered tin oxide in these detectors must be heated, which requires a continuous source of power.

For the foregoing reasons, there is a need for a simple, low cost, low power carbon monoxide detector which operates at ambient temperatures. It is a primary object of the present invention to provide a carbon monoxide detector which exhibits these properties, as well as a faster response time than any other simple point-source sensor.

SUMMARY OF THE INVENTION

The present invention is directed towards a simple, low cost carbon monoxide sensor which rapidly detects the presence of carbon monoxide at ambient temperatures. A carbon monoxide detector having features of the present invention comprises a catalytic material which achieves oxidation of carbon monoxide to carbon dioxide at relatively low temperatures. The catalytic material which facilitates oxidation in the present invention is from a class of catalytic materials comprising one or more noble metals in combination with a suitable reducible oxide. Since this chemical reaction is exothermic, heat generated upon the oxidation of carbon monoxide at the catalyst surface can be detected by a sensing element in contact with the catalytic material. An increase in temperature, and thus conductance, of the sensing element in relation to a reference element then serves as an indicator of the presence of carbon monoxide in the ambient medium.

DRAWINGS

These and other features, aspects and advantages of the present invention will become better understood with regard to the following description, appended claims, and accompanying drawings where:

DESCRIPTION

Figure 1:
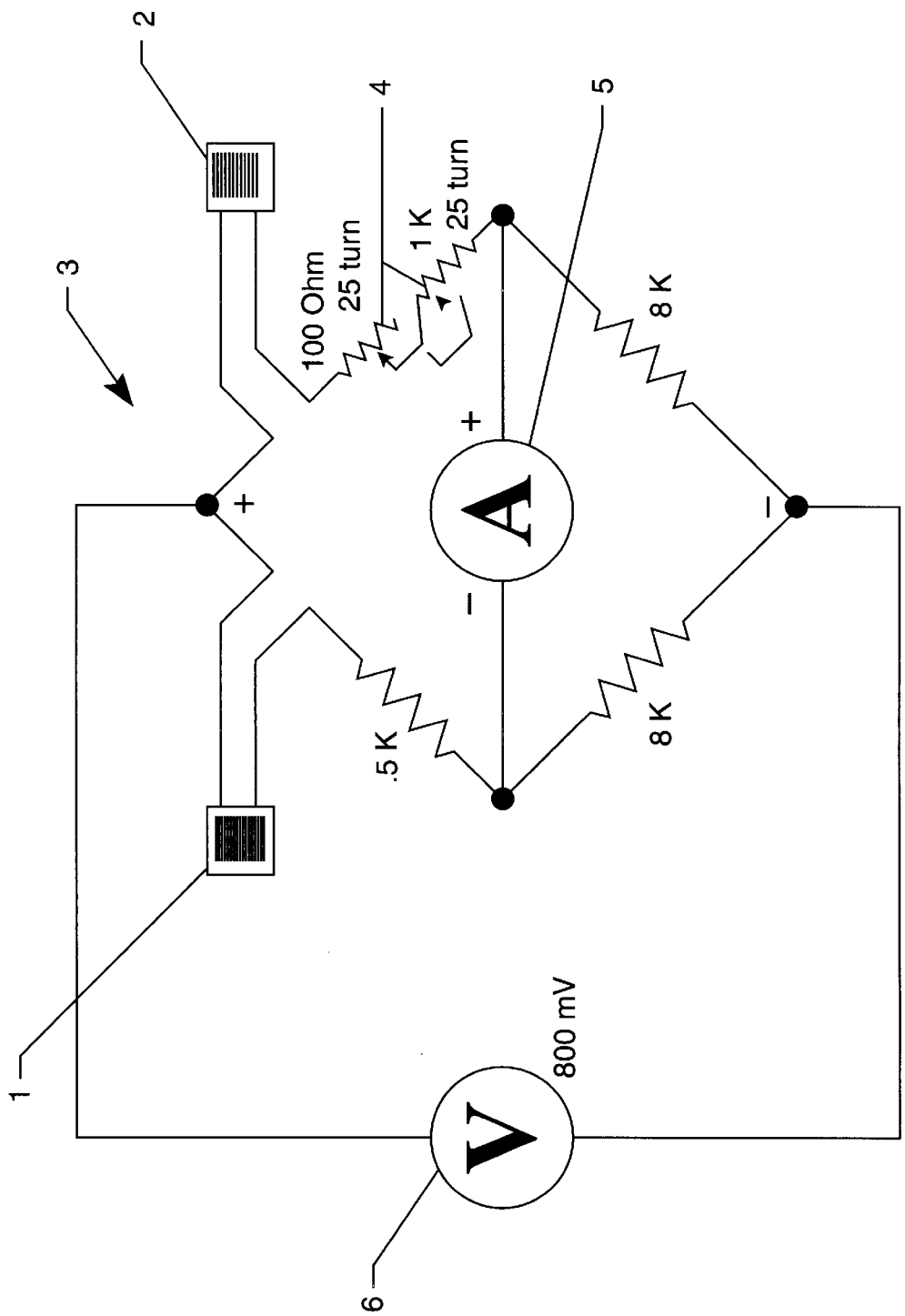
FIG. 1 shows the carbon monoxide sensor.

As shown in FIG. 1, a carbon monoxide sensor comprises a reference thermistor 1 and a sensing thermistor 2 which are attached to opposite legs of a Wheatstone bridge circuit 3. The reference thermistor 1 comprises an uncoated 8 kilo-ohm precision thermistor which is used in the reference leg of the Wheatstone bridge circuit 3 to cancel out any changes in room or gas temperature. The sensing thermistor 2 comprises an 8 kilo-ohm precision thermistor which is surrounded by a catalytic material which exothermically oxidizes carbon monoxide to carbon dioxide at ambient room temperatures. Two trim potentiometers 4 were added to the leg of the bridge circuit containing the sensor to compensate for any differences between the reference and the sensing thermistors.

Within said Wheatstone circuit 3, a nano-ammeter 5 serves to measure the bridge imbalance which occurs upon the change in temperature of the sensing thermistor 2 in relation to the reference thermistor 1. A DC voltage calibrator 6 with a stability of ±10 microvolts is used to apply a signal of 800 millivolts across the Wheatstone bridge circuit.

When in operation, the two thermistors, 1 and 2, remain exposed to the environment of interest so they may respond to concentrations of carbon monoxide and temperature changes in the ambient medium. In the presence of carbon monoxide, the sensing thermistor increases in temperature relative to the reference thermistor due to the exothermic nature of the oxidation of carbon monoxide. Upon an increase in the temperature of the sensing thermistor in relation to the reference thermistor, the two legs of the bridge circuit exhibit different resistances, which generates an electrical current in the Wheatstone bridge circuit 3. The presence and intensity of these currents are detected and reported by the nano-ammeter 5, which thus indicates the presence of carbon monoxide in the ambient medium.

In a preferred version of the present invention, the catalytic material in contact with the sensing thermistor comprises one or more noble metals combined with a reducible oxide. In particular, the sensor which is used in the following example is based on platinized tin-oxide ($Pt/SnO_2$), which is the subject of U.S. Pat. Nos. 4,885,274; 4,912,082; and 4,991,181.

There are many ways in which the method of contact between the sensing thermistor and the catalytic material may be changed within the basic concept of the present invention. In the following example, the sensing thermistor 2 was fabricated by inserting the thermistor leads into a teabag filled with powdered catalyst material and sealing the bag. However, many other methods for obtaining a high active catalyst surface area in close proximity to the thermistor are also being evaluated.

EXAMPLE 1

Sensor Response to Calibration Gases Containing Known Concentrations of Carbon Monoxide Four calibration gases containing 50, 100, 100, and 500 ppm carbon monoxide in air were used to establish the response of the sensor. A cylinder of dry air was used to purge the system and to zero the sensor before and after each run. A 4-way gas valve was used to select the desired gas. Gas flow-rate was controlled and monitored by using a mass flow controller calibrated for air. A needle valve was placed upstream from the flow controller to prevent the flow from exceeding the capacity of the controller. Data were acquired on a 286 computer that used a IEEE bus to communicate with the nanoammeter and flow rate monitor. Data was collected every 10 seconds and smoothed using a three point running average. Upon initiation of run, elapsed run time, bridge current, flow rate, and gas type were written as an ASCII data file on diskette. Final data analysis and display were done with a graphing program.

At the start of each run, the sensor probe was allowed to equilibrate with dry air flowing at 30.0 standard cubic centimeters per minute in the system. After the sensor stabilized, the bridge was zeroed using the trim potentiometers. Several data points were taken with pure air flowing and then the gas was switched to one of the carbon monoxide calibration standards while maintaining the same flow rate. Data was typically taken for 20 to 30 seconds at the selected concentration and then switched to another concentration. Finally the gas stream was switched to air to check for zero at the end of the run.

Figure 2:
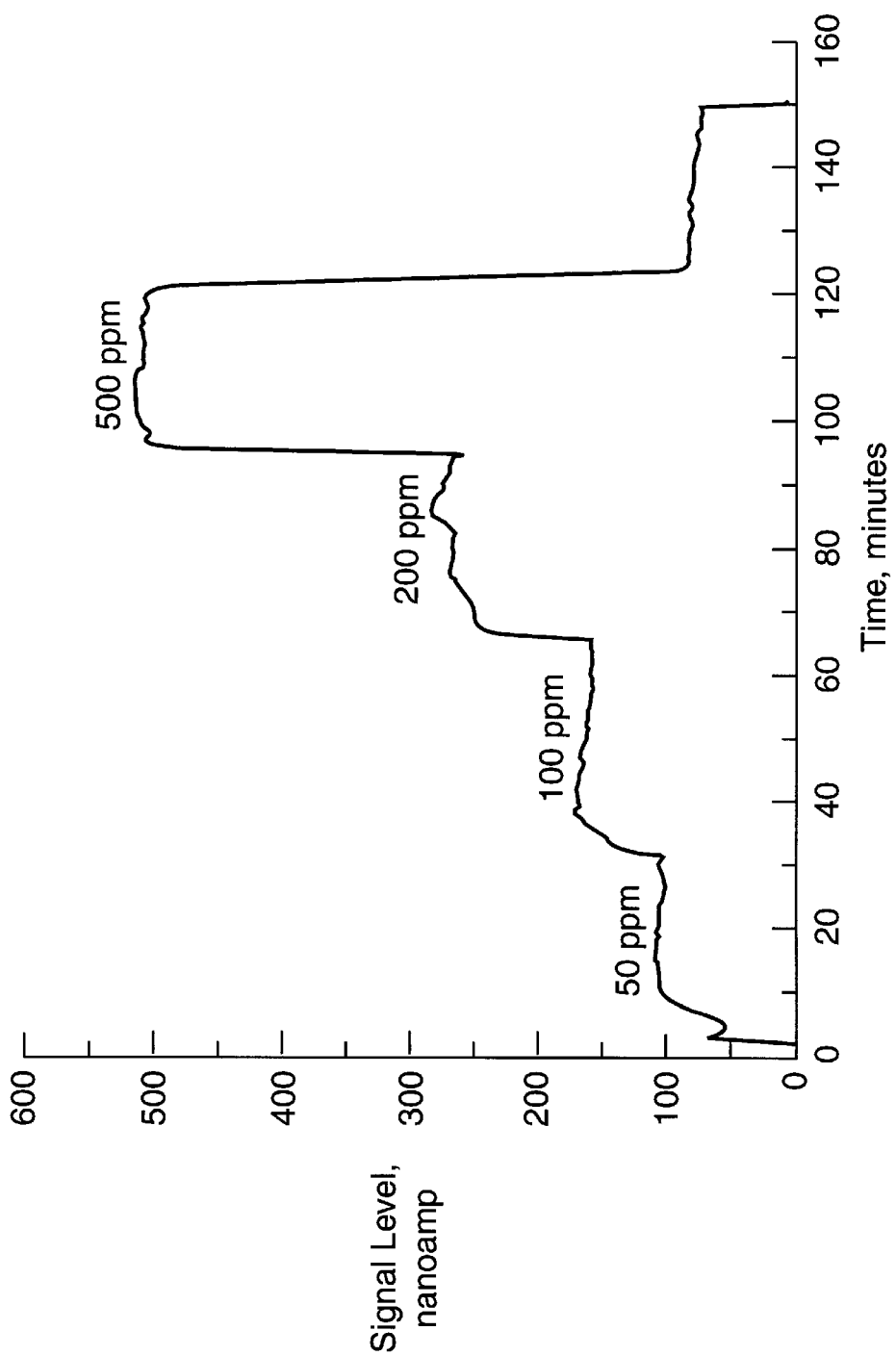
FIG. 2 is a graph showing the response of the carbon monoxide sensor with relation to time and the concentration of carbon monoxide in the air.
Figure 3:
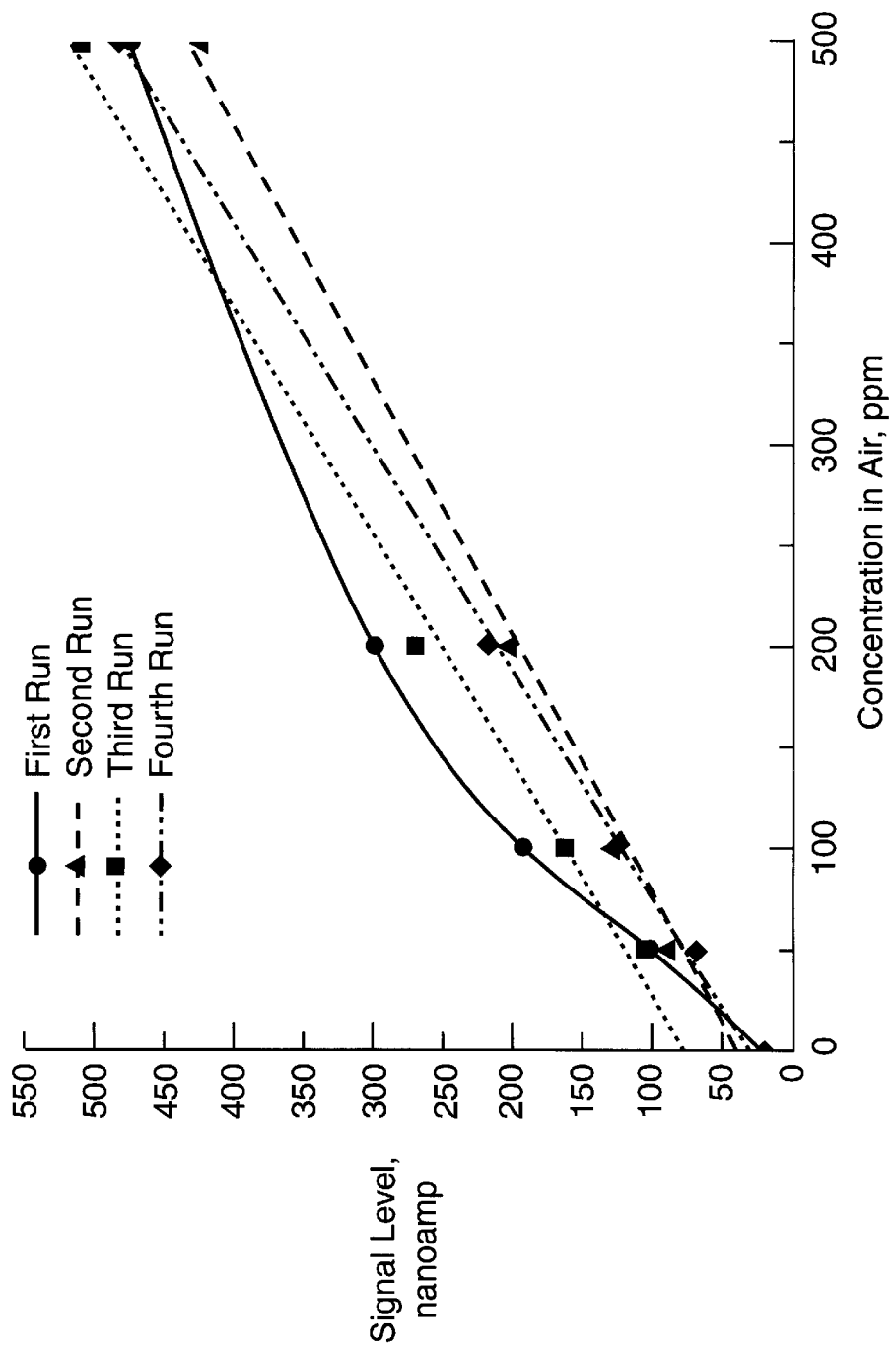
FIG. 3 is a graph showing the sensor response as a function of the concentration of carbon monoxide in air.

In the figures which follow, FIG. 2 provides a good indication of the response time, stability and repeatability of the sensor; FIG. 3 shows the response of a newly fabricated sensor as a function of carbon monoxide concentration for four consecutive runs.

While the invention has been described in terms of its preferred embodiments, those skilled in the art will recognize that the invention can be practiced with modification within the spirit and scope of the appended claims.

We claim:

1. A sensor for detecting the presence of carbon monoxide at ambient temperatures in the atmosphere, or other oxidant-containing media by measuring the change in enthalpy according to a change in temperature of a coated sensing thermistor as the carbon monoxide is converted into carbon dioxide, comprising an uncoated reference thermistor and a coated sensing thermistor.

2. The sensor of claim 1, wherein the reference thermister is an uncoated 8 kilo-Ohm thermister and the sensing thermister is a 8 kilo-Ohm thermister which is coated with an unheated catalytic material which exothermically oxidizes carbon monoxide to carbon dioxide.

3. The sensor of claim 1, wherein said unheated catalytic material comprises one or more noble metals combined with a reducible oxide.

4. The sensor of claim 2, wherein said unheated catalytic material comprises one or more noble metals combined with a reducible oxide.

5. The sensor of claim 1, wherein said catalytic material is in powdered, granular or monolithic form.

6. The sensor of claim 2, wherein said catalytic material is in powdered, granular or monolithic form.

* * * * *

UNITED STATES PATENT AND TRADEMARK OFFICE
CERTIFICATE OF CORRECTION

PATENT NO. : 5,948,965
DATED : September 7, 1999
INVENTOR(S) : Billy T. Upchurch et al.

It is certified that error appears in the above-identified patent and that said Letters Patent is hereby corrected as shown below:

On the Title page

[73] Assignee:

The Government of the United States as represented By the Administrator of the National Aeronautics and Space Administration (NASA) Washington, DC Rochester Gas and Electric Corporation, Rochester, NY Signed and Sealed this First Day of May, 2001

Attest:

NICHOLAS P. GODICI

Attesting Officer

Acting Director of the United States Patent and Trademark Office